United States Patent [19]

Goldstein et al.

[11] Patent Number: 4,547,489

[45] Date of Patent: Oct. 15, 1985

[54] CONFORMATIONALLY RESTRICTED THYMOPENTIN-LIKE COMPOUNDS

[75] Inventors: Gideon Goldstein, Short Hills; George Heavner, Flemington; Tapan Audhya, Bridgewater; Foe-Siong Tjoeng, Neshanic Station, all of N.J.

[73] Assignee: Ortho Pharmaceutical Corporation, Raritan, N.J.

[21] Appl. No.: 618,968

[22] Filed: Jun. 11, 1984

[51] Int. Cl.$^4$ .................... A61K 37/00; C07C 103/52
[52] U.S. Cl. ............................ 514/11; 260/112.5 R
[58] Field of Search ................ 260/112.5 R; 424/177

[56] References Cited

U.S. PATENT DOCUMENTS

| | | | |
|---|---|---|---|
| 4,002,740 | 1/1977 | Goldstein et al. | 260/112.5 R |
| 4,077,949 | 3/1978 | Goldstein | 260/112.5 R |
| 4,190,646 | 2/1980 | Goldstein et al. | 424/177 |
| 4,261,886 | 4/1981 | Goldstein et al. | 260/112.5 R |
| 4,361,673 | 11/1982 | McGregor | 260/112.5 R |
| 4,420,424 | 12/1983 | Geiger et al. | 260/112.5 R |

Primary Examiner—Delbert R. Phillips
Attorney, Agent, or Firm—Geoffrey G. Dellenbaugh

[57] ABSTRACT

Immunoregulating peptides are disclosed which are cyclic peptides similar to thymopentin. These peptides are useful for their effects on the immune system, especially the treatment of thymic deficiencies.

9 Claims, No Drawings

CONFORMATIONALLY RESTRICTED THYMOPENTIN-LIKE COMPOUNDS

BACKGROUND OF THE INVENTION

1. Field of the Invention

This invention relates generally to new immunomodulatory peptides and particularly to conformationally restricted compounds similar to the peptide thymopentin.

2. Description of the Art

U.S. Pat. Nos. 4,190,646 and 4,261,886 disclose various pentapeptides having activity similar to the long chain polypeptide known as thymopoietin, which is described in U.S. Pat. Nos. 4,002,740 and 4,077,949. Thymopoietin selectively stimulates the differentiation of T cells. The pentapeptide disclosed in the '646 patent, which has the sequence H-ARG-LYS-ASP-VAL-TYR-OH, is known as the thymopoietin pentapeptide or "thymopentin". The biological activity of certain of these peptides is described in an article by M. E. Weksler, et al., J. Exp. Med. 148: 996–1006 (1978). The above United States patents and article are incorporated herein by reference. U.S. Pat. Nos. 4,361,673 and 4,420,424 also disclose various peptides asserted to have activity similar to thymopoietin. These disclosed peptides are all linear.

The functional relationship between linear peptides and their cyclic forms is not well understood and is certainly not in any way predictable. For example, the linear octapeptide angiotensin II exhibits high pressor activity while the corresponding cyclic octapeptide exhibits little such activity. Other examples are known.

Based upon the proton nmr studies of thymopoietin in solution it is also unexpected that the cyclic peptides of this invention have thymopoietin-like activity. See, for example, N.R. Krishna, et al., Biochemistry, 19, 5557 (1980).

Certain enzyme-resistant immunomodulatory peptides are disclosed in copending application Serial No. 553,281, filed Nov. 18, 1983, which is incorporated herein by reference.

Thymopentin has been shown to exert a modulatory effect on the immune system of animals and humans and is thus useful for treatment of diseases involving defects in immune function, whether such defects are manifested as deficiencies or excesses of immune function. See for example Audhya, T. and Goldstein, G., Int. J. Pept. Protein Res., 22, 568–572 (1983); Aiuti, et al., Lancet 1:551–555 (1983); and Levinsky, et al., in "Primary Immunodeficiency Diseases", Wedgewood, Rosen, and Paul, eds, 19, 273–276 (1983). Reference is made to these articles and to the above-described patents and article for a discussion of other background material and the biological processes involved in the present invention.

The present invention provides conformationally restricted cyclic peptides and peptide compositions which surprisingly possess thymopentin-like activity and thus offer significant advantages in the treatment of immune defects.

SUMMARY OF THE INVENTION

The present invention relates to novel peptides having the following formulas:

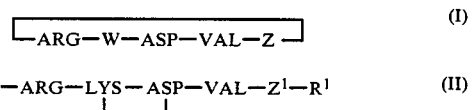

or a pharmaceutically-acceptable acid- or base-addition salt thereof, wherein:

R is H, loweralkyl, formyl, or loweralkanoyl;
W is LYS, PRO, dehydro PRO, or AIB;
Z is TYR, TYR-GLY, PHE, or PHE-GLY;
$Z^1$ is TYR or PHE;
$R^1$ is OH or $NR^2R^3$; and
$R^2$ and $R^3$ are each independently selected from H and loweralkyl.

It has been surprisingly found that the subject peptides possess thymopentin-like activity.

The subject peptides wherein W is PRO, dehydro PRO, or AIB also possess surprising resistance to degradation by enzymes, as disclosed in the above referenced patent application.

DETAILED DESCRIPTION OF THE INVENTION

As indicated above, this invention is concerned with new peptides having thymopoietin-like activity, therapeutic compositions containing these peptides, and methods for use thereof.

In its broadest scope, the present invention provides peptides having the following formula:

$$\boxed{\text{ARG—W—ASP—VAL—Z}} \quad (I)$$

$$R-\text{ARG}-\boxed{\text{LYS}-\text{ASP}-\text{VAL}}-Z^1-R^1 \quad (II)$$

or a pharmaceutically acceptable acid- or base-addition salt thereof, wherein R, W, Z, and $R^1$ are as defined above. The line between ARG and Z in formula (I) and between LYS and ASP in formula (II) indicates an amide bond.

Preferred peptides of the present invention are those of Formula (I) wherein W is LYS. More preferred peptides are those of Formulas I and II wherein R is hydrogen, $R^1$ is OH, W is LYS, Z is TYR or TYR-GLY, and $Z^1$ is TYR. Specific preferred peptides are cyclo-(ARG-LYS-ASP-VAL-TYR), peptide 1; cyclo-(ARG-LYS-ASP-VAL-TYR-GLY), peptide 2; and H-ARG cyclo-(LYS-ASP)-VAL-TYR-OH, peptide 4.

As used herein, the term "loweralkyl" includes branched and straight-chain saturated hydrocarbons having from one to six carbon atoms, such as methyl, ethyl, propyl, isopropyl, pentyl, hexyl, and the like, while the term "loweralkanoyl" means

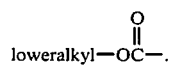

As acids which are able to form salts with these peptides there may be mentioned inorganic acids such as hydrochloric acid, hydrobromic acid, perchloric acid, nitric acid, thiocyanic acid, sulfuric acid, phosphoric acid, and the like, and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalenesulfonic acid, sulfanilic acid, or the like.

As bases which are able to form salts with these peptides, there may be mentioned inorganic bases such as sodium hydroxide, ammonium hydroxide, potassium hydroxide, and the like, and organic bases such as mono-, di-, and trialkyl and aryl amines (e.g., triethylamine, diisopropylamine, methylamine, dimethylamine, and the like) and optionally substituted ethanolamines (e.g., ethanolamine, diethanolamine, and the like).

Throughout this disclosure, the amino acid components of the peptides and certain materials used in their preparation are identified by abbreviations for convenience. These abbreviations are as follows:

| Amino Acid | Abbreviation |
|---|---|
| L-arginine | ARG |
| L-aspartic acid | ASP |
| Glycine | GLY |
| L-lysine | LYS |
| α-methylalanine | AIB |
| L-phenylalanine | PHE |
| L-proline | PRO |
| Dehydroproline | dehydro PRO |
| L-tyrosine | TYR |
| L-valine | VAL |

The peptides of the invention may generally be prepared following known techniques. Conveniently, the peptides may be prepared following the solid-phase synthetic technique initially described by Merrifield in JACS, 85, 2149-2154 (1963). Such methods are also disclosed in certain of the prior art patents referred to above. Other techniques may be found, for example, in M. Bodanszky, et al., *Peptide Synthesis*, John Wiley & Sons, second edition, 1976, as well as in other reference works known to those skilled in the art. Appropriate protective groups usable in such syntheses and their abbreviations will be found in the above text, as well as in J. F. W. McOmie, *Protective Groups in Organic Chemistry*, Plenum Press, New York, 1973. Both of these books are incorporated herein by a reference. The common protective groups used herein are t-butyloxycarbonyl (BOC), benzyl (BZL), t-amyloxycarbonyl (AOC), tosyl (TOS), c-bromophenylmethoxycarbonyl (BrZ), 2-6-dichlorobenzyl (BZLCl2), and phenylmethoxycarbonyl (Z or CBZ).

The peptides of this invention have been found to exhibit biological activity similar to thymopoietin, as disclosed in the above-referenced United States patents and articles. This biological activity is evidenced by an assay measuring induction of cyclic-GMP production in a human T-cell line in comparison with thymopoietin. The induction of c-GMP production by a test peptide in this assay indicates the ability of the test peptide to bind to the thymopoietin receptor site on the cell and induce thymopoietin-like biological activity.

The biological activity of the subject peptides is also indicated by the binding of these peptides to the cell membrane receptor for the active site of thymopoietin.

Prior to the making of the present invention, it was completely unexpected that one would be able to prepare such cyclic peptides having thymopentin-like activity. The nmr study reference described above generally indicates that a strong interaction between the guanidino group of L-arginine and the beta-carboxylate group of L-aspartic acid is a conformationally stabilizing factor for thymopentin in solution and has been suggested to be related to biological activity. The subject compounds, because of their conformationally-restricted nature, cannot assume the preferred solution conformation exhibited by thymopentin and thus cannot exhibit this interaction. Based upon the Krishna reference, therefore, one would not expect the subject compounds to exhibit thymopoietin-like activity, as in fact they do. Contrariwise, base upon the Krishna reference one would expect activity for

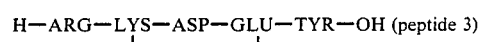
H—ARG—LYS—ASP—GLU—TYR—OH (peptide 3)

(which can assume the preferred conformation); it was found to be inactive.

Because of the immunomodulatory characteristics of the subject peptides, they are therapeutically useful in the treatment of humans and animals, since they have the capability for inducing the differentiation of lymphopoietic stem cells in the haemopoietic tissues into thymus-derived cells (T cells) which are capable of involvement in the immune response of the body. As a result, the subject peptides are considered to have multiple therapeutic uses.

Primarily, since the compounds have the capability of carrying out certain of the indicated functions of the thymus, they have application in various thymic function and immunity areas. One such application is in the treatment of DiGeorge Syndrome, a condition in which there is congenital absence of the thymus. Administration of one of the subject peptides to a sufferer from DiGeorge Syndrome will assist in overcoming this deficiency. Those of skill in the immunological art can readily determine the appropriate route for administration (preferably parenterally) and can determine the effective amount of one of the subject peptides for treatment of Digeorge Syndrome. Because the subject peptides are more potent than thymopentin, they are more therapeutically useful than prior art peptides.

Additionally, the subject peptides are considered useful in assisting the collective immunity of the body, in that they will increase or assist in therapeutic stimulation of cellular immunity and thereby are useful in the treatment of diseases involving chronic infection, such as fungal or mycoplasma infections, tuberculosis, leprosy, acute and chronic and viral infections and the like.

The subject compounds are generally considered to be useful in any area in which cellular immunity is an issue and particularly where there are deficiencies in immunity such as in the DiGeorge syndrome mentioned above. Thus, where there is an excess of antibody production due to unbalanced T cells and B cells, the subject peptides can correct this condition by stimulating T cell production. Thus, they are expected to be of therapeutic use in certain autoimmune diseases in which damaging antibodies are produced, such as systemic lupus erythematosis, rheumatoid arthritis, or the like.

In their broadest application, the subject compounds are useful for regulating the immune system of a subject, human or animal, in need of such regulation. As used herein, the term "regulate" means that the subject compounds cause the immune system to return from an abnormal, diseased state to a normal, balanced state. While this regulation may well find great application in the correction of immunological deficiencies (e.g., DiGeorge syndrome), it is also applicable to correct conditions of excess immunological activity (e.g., autoimmune diseases). The present invention therefore includes methods for regulating the immune system of a subject in need of such regulation which comprises administering to said subject an immunoregulatorily-effective amount of one of the subject compounds, as well as pharmaceutical compositions for practicing these methods.

The present invention provides a method for treatment of conditions resulting from relative or absolute T cell deficiencies in a subject (human or animal) having such a condition which comprises administering to the subject a therapeutically-effective amount of a peptide of formula (I) or (II). The invention also provides a method for treatment of conditions resulting from relative or absolute deficiencies of the thymus of a subject which comprises administering to said subject a therapeutically-effective amount of a peptide of formula (I) or (II). As used herein, the term "therapeutically-effective amount" means an amount which is effective to treat conditions resulting from T cell deficiencies, or deficiencies of the thymus, respectively. The invention also provides a method for inducing lymphopoietic stem cells of a subject to develop the characteristics of thymus-derived lymphocytes which comprises administering to the subject an effective inducing amount of a peptide of formula (I) or (II). The invention further provided pharmaceutical compositions for practicing those methods.

To prepare the pharmaceutical compositions of the present invention, a peptide of formula (I) or (II) or a base or acid addition salt thereof is combined as the active ingredient in intimate admixture with a pharmaceutical carrier according to conventional pharmaceutical compounding techniques. This carrier may take a wide variety of forms depending on the form of preparation desired for administration, e.g., sublingual, rectal, nasal, oral, or parenteral. In preparing the compositions in oral dosage form, any of the usual pharmaceutical media may be employed, such as for example, water, oils, alcohols, flavoring agents, preservatives, coloring agents and the like in the case or oral liquid preparation (e.g., suspensions, elixirs, and solutions) or carriers such as starches, sugars, diluents, granulating agents, lubricants, binders, disintegrating agents, and the like in the case of oral solid preparations (e.g., powders, capsules, and tablets). Controlled release forms may also be used. Because of their ease in administration, tablets and capsules represent the most advantageous oral dosage unit form, in which case solid pharmaceutical carriers are obviously employed. If desired, tablets may be sugar coated or enteric coated by standard techniques.

For parenteral products, the carrier will usually comprise sterile water, although other ingredients to aid solubility or for preservation purposes (for example) may be included. Injectable suspensions may also be prepared, in which case appropriate liquid carriers, suspending agents, and the like may be employed.

The subject peptides are generally active when administered parenterally in amounts above about 1µg/kg of body weight. For treatment of DiGeorge Syndrome, the peptides may be administered parenterally from about 0.1 to about 10 mg/kg body weight. Generally, the same range of dosage amounts may be used in treatment of the other diseases or conditions mentioned where immunodeficiency is to be treated. Larger amounts (e.g., about 10–1000 mg/kg body weight) are useful for suppressing excess immune activity.

The following examples are presented to illustrate the invention without intending specifically limiting the invention thereto. In the examples and throughout the specification, parts are by weight unless otherwise indicated. The title peptide in each Example is referred to by number in parentheses following the formula; these numbers are used to refer to the respective peptides in subsequent Examples.

EXAMPLE I

Boc-Tyr(Bzl)-OMP (5). Potassium fluoride (2.0 g, 35 mmol) was added to a solution of (4-methoxy)phenacyl bromide (3.76 g, 16 mmol) and Boc-Tyr(Bzl) (5.57 g, 15 mmol) in acetonitrile (60 ml) and the mixture stirred for 36 hr at ambient temperature. The solids were removed by filtration. Ethyl acetate (150 ml) and H$_2$O (150 ml) were added to the filtrate. The organic phase was removed and the aqueous phase was reextracted with ethyl acetate (3×30 ml). The combined organic phases were washed with water (2×150 ml), saturated sodium bicarbonate (3×150 ml), and water (3×150 ml) and dried over sodium sulfate. The drying agent was removed by filtration and the solvent was removed under reduced pressure. The resulting oil was triturated with petroleum ether. The solid was filtered off and dried under reduced pressure to give 7.70 grams (98.8 percent) of 5, m.p. 102°–105° C.

Anal. calcd for $C_{30}H_{33}NO_7H_2O$: C, 67.02; H, 6.56; N, 2.61. found: C, 66.97; H, 6.17; N, 2.61.

EXAMPLE II

HCl Tyr(Bzl)-OMP (6). Boc-Tyr(Bzl)OMP (7.2 g, 14 mmol) was added to 100 ml 4 N HCl/dioxane and stirred at ambient temperature for 45 min. The solution was evaporated to dryness to give 4.96 g (85.7 percent) of a white solid.

Anal. calcd for $C_{25}H_{26}NO_5Cl.2H_2O$: C, 64.44; H, 6.48; N, 3.01. found: C, 64.61; H, 5.74; N, 3.20.

EXAMPLE III

Boc-Val-Tyr(Bzl)-OMP (7). In a 250 ml 3-neck flask fitted with a drying tube, Boc-valine-OH (2.6 g, 12 mmol) and N-methylmorpholine (4.1 g, 10.8 mmol) were dissolved in ethyl acetate (20 ml) and cooled to −15° C. Isobutylchloroformate (1.5 ml, 10.8 mmol) was added dropwise over 10 min while the temperature was maintained at −20 to -15° C. Stirring was continued at this temperature for 20 min. A precooled solution of 6 (4.21 g, 10 mmol) and N-methylmorpholine (1.09 g, 10.8 mmol) in ethyl acetate (20 ml) and DMF (20 ml) was added over 10 min. The reaction mixture was stirred at −10° C. for 5 hrs and stored in refrigerator overnight. Solids were removed by filtration and the filtrate washed with water (3×), saturated sodium bicarbonate (3×), water (3×), IN hydrochloric acid (3×) and water (3×) and dried over anhydrous sodium sulfate. The drying agent was removed by filtration and the solvent was removed under reduced pressure t give 4.7 g (91 percent) of 7 as a white solid, m.p. 150°–153° C.

Anal. calcd for $C_{35}H_{42}N_2O_8$: C, 67.94; H, 6.84; N, 4.52. found: C, 67.57; H, 6.80; N, 4.40.

EXAMPLE IV

HCl Val-Tyr(Bzl)-OMP (8). To 150 ml of 4.5 N HCl/dioxane was added Boc-Val-Tyr(Bzl)-OMP (10 7 g, 20 mmol). The mixture was stirred at ambient temperature for 1 hr. The solvent was removed under reduced pressure and the residue triturated with diethylether. The solid was removed by filtration and under reduced pressure to give 9.01 g (70.6) of 8 as a white solid.

Anal. calcd for $C_{30}H_{34}N_{2}O_{6}HCl$: C, 66.84; H, 6.55; N, 5.19. found: C, 63.33; H, 6.42; N, 4.61.

EXAMPLE V

Boc-Gly-OMP (9). A suspension of potassium fluoride (5.08 g, 80 mmol), (4-methoxyphenacyl)bromide (9.4, 40 mmol) and Boc glycine (5.6 g, 30 mmol) in acetonitrile (120 ml) was stirred for 36 hr at ambient temperature. The solid material was removed by filtration. Ethyl acetate (150 ml) and water (150 ml) were added to the filtrate. The aqueous layer was removed and extracted with ethyl acetate (3×30 ml). The combined organic phases were washed with water (2×150 ml), saturated sodium bicarbonate (3×150 ml), and water (3×150 ml) and dried over anhydrous sodium sulfate. The drying agent was removed by filtration and the filtrate evaporated to dryness under reduced pressure to give an oil which solidified upon the addition of petroleum ether to give 11.95 grams of 9 (92.4 percent); m.p. 75°–77°.

Anal. calcd for $C_{16}H_{21}O_{6}N$: C, 59.45; H, 6.55; N, 4.33. found: C, 59.03; H, 6.47; N, 4.20.

EXAMPLE VI

HCl Gly-OMP (10). Boc-Gly-OMP (9.9 g, 31 mmol) was added to 100 ml of 4.5 N HCl in dioxane and stirred at ambient temperature for one hour. The resulting solid was removed by filtration, washed well with ether and dried under reduced pressure to give 7.8 grams of 10 (96.89 percent).

Anal. calcd for $C_{11}H_{14}O_{4}Cl$: C, 50.88; H, 5.43; N, 5.39. found: C, 51.09; H, 5.41; N, 5.57.

EXAMPLE VII

Boc-Tyr(Bzl)-Gly-OMP (11). In a 250 ml 3-neck flask fitted with a drying tube, Box-Tyr(Bzl) (12.3 g, 33 mmol) and N-methyl-morpholine (3.4 ml, 33 mmol) were dissolved in ethyl acetate (60 ml) and cooled to −15°. Isobutylchloroformate (4.2 ml, 33 mmol) was added dropwise over 10 min and the temperature was maintained at −20° to −15° C. After stirring for an additional 20 min, a precooled solution of HCl Gly-OMP (7.8 g, 30 mmol) and N-methylmorpholine (3.4 ml, 33 mmol) in ethylacetate was added dropwise over 10 min. The reaction was stirred at −10° C. for 5 hrs and at 4 overnight. Solids were removed by filtration and the organic phase washed with water (3×), saturated sodium biocarbonate (3×), water (3×), 1N hydrochloric acid (3×) and water (3×). The organic phase was dried over anhydrous sodium sulfate. The drying agent was removed by filtration and the filtrate was removed under reduced pressure to give 11 as a white solid, 14.70 g (89.96 percent) m.p. 119°–122°.

Anal. calcd for $C_{32}H_{36}N_{2}O_{8}$: C, 66.65; H, 6.29; N, 4.99. found: C, 66.79; H, 6.30; N, 4.85.

EXAMPLE VIII

HCl Tyr(Bzl)Gly-OMP (12). Boc-Tyr(Bzl)-Gly-OMP (11) (14 g, 25 mmol) was added to 100 ml of 4.5 N HCl in dioxane and stirred at ambient temperature for 1.5 hr. The addition of either precipitated a solid which was removed by filtration, washed with either and dried under reduced vacuum to give 12.33 grams of 12 (90.5 percent).

Anal. calcd for $C_{27}H_{28}N_{2}O_{8}HCl$: C, 59.50; H, 5.36; N, 5.14. found: C, 61.32; H, 5.57; N, 5.11.

EXAMPLE IX

Boc-Val-Tyr(Bzl)-Gly-OMP (13). Boc-valine (4.78 g, 22 mmol) and N-methylmorpholine (2.23 g, 22 mmol) were dissolved in 20 ml of ethyl acetate and cooled to −15°. Isobutylchloroformate (3.00 g, 22 mmol) was added and the resulting mixture stirred for 20 min at −15° to −20°. A precooled (−5d) solution of 12 (11.5 g, 21 mmol) and N-methylmorpholine (3.14 g, 31 mmol) in dimethylformamide (40 ml) was added to the first solution over 10 minutes. Stirring was continued at −15° to −20° for 5 hr. Solids were removed by filtration. Chloroform was added, and the solution was washed with water (3×), saturated sodium bicarbonate (3×), water (3×) and dried over anhydrous sodium sulfate. Removal of the drying agent by filtration and of the solvent under reduced pressure gave 13.18 g (97 percent) of 13 as a white solid, m.p. 168°–170°.

Anal. calcd for $C_{37}H_{45}N_{3}O_{9}$: C, 65.76; H, 6.71; N, 6.22. found: C, 65.25; H, 6.69; N, 6.27.

EXAMPLE X

HCl Val-Tyr(Bzl)-Gly-OMP (14). Boc-Val-Tyr(Bzl)-Gly-OMP (13) (12 g, 19 mmol) was added to 80 ml of 4 N HCl/dioxane the resulting mixture allowed to stir 1½ hrs at ambient temperature. Diethylether was added the solid was removed by filtration and washed with either and dried under reduced pressure to give 14 as a white solid (6.72 g, 63.16 percent).

Anal. calcd for $C_{31}H_{43}N_{3}O_{6}HCl$: C, 63.19; H, 7.36; N, 7.13. found: C, 60.86; H, 6.10; N, 6.54.

EXAMPLE XI

Boc-Asp(OBzl)-OMP (15). Potassium fluoride (2.03 g, 35 mmol) was added to a solution of (4-methoxy)-phenacyl bromide (3.76 g, 16 mmol) and Boc-Asp(OBzl) (4.45 g, 15 mmol) in acetonitrile (60 ml) and stirred for 36 hr at ambient temperature. The solids were removed by filtration. Ethyl acetate (150 ml) and water (150 ml) were added to the filtrate. The phases were separated and the aqueous phase was reextracted with ethyl acetate (3×30 ml). The combined organic phases were washed with water (2×150 ml), saturated sodium bicarbonate (3×150 ml), water (3×150 ml) and dried over anhydrous sodium sulfate. The drying agent was removed by filtration and the solvent removed under reduced pressure to give 32.95 g (97 percent) of 15 as a white solid, m.p. 95°–96° C.

Anal. calcd for $C_{25}H_{29}NO_{8}$ C, 63.68; H, 6.19; N, 2.97. found: C, 63.11; H, 6.15; N, 2.87.

EXAMPLE XII

HCl Asp-(OBzl)-OMP (16). To 250 ml 4 N HCl in dioxane was added Boc-Asp(OBzl)-OMP (15) (32.95 g, 69 mmol). The reaction was stirred for 1.5 hr at ambient temperature. The resulting solid was removed by filtration, washed with diethylacetate and dried under reduced pressure to give 27.90 g (98 percent) of 16.

Anal. calcd for $C_{20}H_{22}NO_{6}Cl \cdot 3H_{2}O$: C, 52.01; H, 6.11; N, 3.03. found: C, 52.13; H, 4.18; N, 2.87.

EXAMPLE XIII

Boc-Lys(Z)-Asp-(OBzl)-OMP (17). Boc-Z-lysine (4.11 g, 10.8 mmol) and N-methylmorpholine (1.1 g, 10.8 mmol) were dissolved in 20 ml of ethylacetate and cooled to −15°. Isobutylchloroformate (1.48 g, 10.8 mmol) was added over 10 min and the resulting mixture stirred for 20 min at −20° to −15°. A precooled solution of 16 (4.0 g, 9.8 mmol) and N-methylmorpholine (1.09 g, 10.8 mmol) in ethylacetate (20 ml) and dimethylformamide (20 ml) was added over 10 min. The reaction mixture was stirred for 5 hr at −20° to −15°. Solids were removed by filtration and the filtrate was washed with water (2×) saturated sodium bicarbonate (3×), water (3×), 1 N hydrochloric acid (3×), water (3×) and dried over anhydrous sodium sulfate. The drying agent was removed by filtration and the solvent removed under reduced pressure to give 4.74 g (66 percent) of 17 as a white solid, m.p. 55°–57°.

Anal. calcd for $C_{39}H_{47}N_3O_{11}$: C, 63.84; H, 6.46; N, 5.73. found: C, 63.65; H, 6.51; N, 5.47.

EXAMPLE XIV

HCl Lys(Z)-Asp(OBzl)-OMP (18). Boc-Lys(Z)-Asp(OBzl)-OMP (17) (44.0 g, 60 mmol) was added to 150 ml of 4.5 N HCl in dioxane and stirred at ambient temperature for 1.5 hr. The product was precipitated by the addition of ether, removed by filtration, washed with ether and dried under reduced pressure to give 36.3 g (90 percent) of 18.

Anal. calcd for $C_{34}H_{39}N_3O_9HCl$: C, 60.94; H, 6.02; N, 6.27. found: C, 59.97; H, 5.98; N, 6.06.

EXAMPLE XV

Aoc-Arg(Tos)-Lys(Z)-Asp(OBzl)-OMP (19). HCl Lys(Z)-Asp(OBzl)-OMP (18) (5.3 g, 8 mmol) was dissolved in methylene chloride with a small amount of dimethylformamide. The mixture was cooled. Diisopropylethylamine (1.03 g, 8 mmol) was added and the reaction mixture stirred for 15 min. Aoc-Arg(Tos) (5.2 g, 12 mmol) dissolved in methylene chloride with a small amount of dimethylformamide and added to the first solution, followed by the addition of 1-hydroxybenzotriazole hydrate HOBt (1.6 g, 12 mmol). After stirring for 20 min, dicyclohexylcarbodiimide (2.5 g, 12 mmol) was added and the reaction mixture stirred overnight, allowing the temperature to rise to ambient. The solids were removed by filtration and the solvent removed under reduced pressure to give a yellow oil. The oil was dissolved in ethylacetate, washed with water (3×100 ml) and dried over anhydrous sodium sulfate. The drying agent was removed by filtration and the solvent was removed under reduced pressure to give a residue which solidified to give 7.45 g (87 percent) of 19 as an off white solid, m.p. 60°–63°.

Anal. calcd for $C_{53}H_{69}N_7O_{14}S$: C, 60.04; H, 6.56; N, 9.25. found: C, 59.60; H, 6.61; N, 9.75.

EXAMPLE XVI

Aoc-Arg(Tos)-Lys(Z)-Asp(OBzl) (20). Aoc-Arg(Tos)-Lys(Z)-Asp (OBzl)-OMP (6.18 g; 5.75 mmol) was dissolved in 85 percent aqueous acetic acid (200 ml). Zn dust (20 g) was added portion-wise over a period of 4 h. The reaction mixture was stirred for 2 days at ambient temperature. Solids were removed by filtration and water (600 ml) was added to the filtrate. The pH was adjusted to 2.5 with 2N HCl. This solution was extracted with ethylacetate/tetrahydrofuran (65:35; 3×500 ml). The combined organic phases were washed with water (3×400 ml) and dried over anhydrous sodium sulfate. The drying agent was removed by filtration and the filtrate was evaporated to dryness under reduced pressure. The residue was dissolved in ethylacetate (30 ml) and added dropwise to 800 ml of diethylether with stirring. After cooling to 4° overnight the solid was removed by filtration and dried over $P_2O_5$ under reduced pressure to give 4.4 g (83 percent) of 20; $R_f$ 0.8 (A); m.p. 84–87° C.

Anal. calcd for $C_{44}H_{59}N_7O_{12}S.H_2O$: C, 56.94; H, 6.62; N, 10.56. found: C, 56.70; H, 6.43; N, 10.69.

EXAMPLE XVII

Aoc-Arg(Tos)-Lys(Z)-Asp(OBzl)-Val-Tyr(Bzl)-OMP (21). HCl Val-Tyr(Bzl)-OMP (8) (2.8 g; 4.5 mmol) was dissolved in dimethylformamide (40 ml) and cooled in an ice bath. Diisopropylethylamine (0.95 ml; 5.5 mmol) was added dropwise, followed by Aoc-Arg-(Tos)-Lys(Z)-Asp(OBzl) (20) (4.4 g; 48 mmol), 1-hydroxybenzotriazole (0.7 g; 5 mmol) and dicyclohexylcarbodiimide (1.03 g; 5 mmol). The reaction mixture was stirred for 1 h at 0° C. and 3 days at ambient temperature. Solids were removed by filtration and the solvent was removed under reduced pressure. The residue was dissolved in chloroform and washed with 0.5 N hydrochloric acid (3×200 ml), saturated sodium bicarbonate (3×200 ml), water (200 ml) and dried over anhydrous sodium sulfate. The drying agent was removed by filtration and the filtrate was evaporated under reduced pressure. The residue was dissolved in dimethylformamide/chloroform (30 ml; 1:1) and added dropwise to 800 ml of diethylether. After cooling to 4° C. overnight the solid was removed by filtration and dried over $P_2O_5$ under reduced pressure to give 6.52 g (95 percent) of 21; $R_f$ 0.9 (B). Amino acid analysis: Asp, 1.11; Val, 1.07; Tyr, 0.90; Lys, 0.93 and Arg, 0.99.

EXAMPLE XVIII

Aoc-Arg(Tos)-Lys(Z)-Asp(OBzl)-Val-Tyr(Bzl) (22). Aoc-Arg(Tos)-Lys(Z)-Asp(OBzl)-Val-Tyr(Bzl)-OMP (6.5 g; 4.6 mmol) was dissolved in 85% aqueous acetic acid (300 ml). Zn dust (25 g) was added portion-wise over 24 hours. Water (600 ml) was added and the reaction mixture cooled. The mixture was stirred for 2 days at ambient temperature and at 4° C. overnight. The solids were removed by filtration and washed well with diethylether. The solids were suspended (3×) in dimethylformamide (50 ml) and filtered. The combined dimethylformamide extracts were concentrated to 50 ml under reduced pressure and added dropwise to diethylether (1000 ml). The precipitate was filtered, washed with ether and dried under reduced pressure to give 5.65 g (96 percent) of 22; $R_f$ 0.85 (B); pmr (DMSO-$d_6$): absence of p-methoxyphenacyl protons.

EXAMPLE XIX

HCl Arg(Tos)-Lys(Z)-Asp(OBzl)-Val-Tyr(Bzl) (23). Aoc-Arg(Tos)-Lys(Z)-Asp(OBzl)-Val-Tyr(Bzl) (22) (3.5 g; 2.77 mmol) was treated with 4N HCl/dioxane (200 ml) for 1 h. The solvent was removed under reduced pressure and the residue dissolved in dimethylformamide (20 ml). This solution was added into ether (700 ml) dropwise with stirring and the mixture was cooled at 4° overnight. The solid was filtered off and dried over $P_2O_5$ under reduced pressure to give 3.3 g (100 percent) of 23; $R_f$ 0.7 (B); pmr (DMSO-$d_6$); signals for Aoc-group disappeared. This material was used without further purification.

EXAMPLE XX

Cyclo-[Arg(Tos)-Lys(Z)-Asp)(OBzl)-Val-Tyr(Bzl)] 24). HCl Arg-(Tos)-Lys(Z)-Asp(OBzl)-Val-Tyr(Bzl) (3.2 g; 2.7 mmol) was dissolved in dimethylformamide (1300 ml) and the pH of the solution was adjusted to 7.5 with diisopropylethylamine. The reaction mixture was cooled to $-25°$ C. and diphenylphosphorylazide (0.75 ml) was added dropwise with stirring. The solution was stirred at 4° C. for 7 days while the pH was kept at 7.5. The solvent was removed under reduced pressure and the residue was triturated with water. The solid was filtered off and dried over $P_2O_5$ under reduced pressure to give 3 g of crude 24, which was used without further purification; $R_f 0.85(B)$.

EXAMPLE XXI

Cyclo-(Arg-Lys-Asp-Val-Tyr) (1). The crude Cyclo-[Arg(Tos)-Lys(Z)-Asp(OBzl)-Val-Tyr(Bzl)] (1 g) was cleaved with 20 ml of HF containing 2 ml anisole at 0° C. for 1 h. The peptide/resin mixture was washed with ether (3×20 ml). The free peptide was extracted with 5 HOAc/H$_2$O (3×20 ml) and lyophilized. The crude material was applied on Sephadex SPC-25 column (60 cm×2.5 cm) previously equilibrated with 0.1M NH$_4$OAc, pH 5. The column was eluted with the equilibration buffer at a flow rate of 85 ml/h and fractions of 13 ml were collected. After 2, the buffer was replaced with 0.2M NH$_4$OAc, pH 6.5. Fractions 201–219 were pooled and lyophilized to give 75 mg of product; $R_f$ 0.3 (C); Amino acid analysis: acid hydrolysis: Arg, 103; Lys, 1.02; Asp, 1.03; Val, 0.99; Tyr, 0.92; Leucine amino peptidase: traces (<1.7) of Arg and Lys; FAB/MS: MH+ 662; HPLC: $C_{18}$-μBondapak column, 10 percent methanol/90 percent 0.02M KH$_2$PO$_4$, pH 3.5, 2 ml/min, 214 nm, elution time 40.67 min.

EXAMPLE XXII

Aoc-Arg(Tos)-Lys(Z)-Asp(OBzl)-Val-Tyr(Bzl)-Gly-OMP (25). HCl Val-Try(Bzl)-Gly-OMP (14) (3.1 g; 5 mmol) was dissolved in dimethylformamide (40 ml) and cooled in an ice bath. Dissopropylethylamine (0.95 ml; 5.5 mmol) was added dropwise with stirring, followed by Aoc-Arg(Tos)-Asp(OBzl)-Val (20) (4.55 g; 5 mmol), 1-hydroxybenzotriazole hydrate (0.77 g; 5.5 mmol) and dicyclohexylcarbodiimide (1.03 g; 5 mmol). The reaction mixture was stirred for 3 days at ambient temperature. Solids were removed by filtration and the solvent was removed under reduced pressure. The residue was dissolved in chloroform and washed with 0.5N hydrochloric acid (3×200 ml), saturated sodium bicarbonate (3×200 ml), water (2.00 ml) and dried over anhydrous sodium sulfate. The drying agent was removed by filtration and the filtrate evaporated under reduced pressure. The residue was dissolved in dimethylformamide/chloroform (30 ml; 1:1) and added dropwise to 800 ml of diethylether. After cooling to 4° overnight, the solid was filtered off and dried over $P_2O_5$ under reduced pressure to give 4.51 g (62 percent); $R_f 0.85(B)$. Amino acid analysis: Asp, 1.07; Gly, 0.96; Val, 1.09; Tyr, 0.91; Lys, 0.87; Arg, 1.10.

EXAMPLE XXIII

Aoc-Arg(Tos)-Lys(Z)-Asp(OBzl)-Val-Tyr(Bzl)-Gly (26). Aoc-Arg(Tos)-Lys(Z)-Asp(OBzl)-Val-Tyr(Bzl)-Gly-OMP (25) (4.5 g; 3.07 mmol) was reduced with Zn dust (25 g) in 85 percent aqueous acetic acid (300 ml) for 3 days. Water (600 ml) was added and the reaction mixture was cooled to 4° overnight. The solids were filtered off and washed with diethylether. The solids were slurried (3×) in dimethylformamide (50 ml) and filtered. The combined filtrates were concentrated to 50 ml under reduced pressure and added dropwise to diethylether (1000 ml). The precipitate was collected by filtration and dried under reduced pressure to give 3.77 g (93 percent) of 26. pmr (DMSO-d$_6$) showed absence of p-methoxyphenacyl protons.

EXAMPLE XXIV

HCl Arg(Tos)-Lys(Z)-Asp(OBzl)-Val-Tyr(Bzl)-Gly (27). Aoc-Arg(Tos)-Lys(Z)-Asp(OBzl)-Val-Tyr(Bzl)-Gly (26) (3.5 g; 2.65 mmol) was treated with 4N HCl/dioxane (200 ml) for 1 h. The solvent was removed under reduced pressure and the residue was dissolved in dimethylformanide (30 ml) and added dropwise to diethylether (800 ml) with stirring. The mixture was cooled to 4° overnight. The resulting solid was removed by filtration and dried over $P_2O_5$ under reduced pressure to give 3.30 g (100 percent); $R_f 0.81$ (B); pmr (DMSO-d$_6$) showed no signals for Aoc-group.

EXAMPLE XXV

Cyclo-[Arg(Tos)-Lys(Z)-Asp(OBzl)-Val-Tyr(Bzl)-Gly] (28). HCl Arg(Tos)-Lys(Z)-Asp(OBzl)-Val-Tyr(Bzl)-Gly (27) (3.2 g; 2.57 mmol) was dissolved in dimethylformamide (1300 ml) and the pH of the solution was adjusted to 7.5 with diisopropylethylamine. The reaction mixture was cooled down to $-25°$ C. and diphenylphosphorylazide (0.72 ml) was added slowly with stirring. The mixture was kept for 7 days at 4° C. with occasionally stirring. The pH of the solution was maintained at 7.5 during this period. The solvent was removed uner reduced pressure and the residue was triturated with water. The solid was collected by filtration and dried under reduced pressure to give 2.8 g of product; $R_f 0.87(B)$.

EXAMPLE XXVI

Cyclo-[Arg-Lys-Asp-Val-Tyr-Gly] (2). The crude cyclo[Arg(Tos)-Lys(Z)-Asp(OBzl)-Val-Tyr(Bzl)-Gly] (1 g) was cleaved with HF/anisole (20 ml; 9:1) at 0° C. for 1 h. The peptide resin mixture was washed with diethylether (3×20 ml). The peptide was extracted with 5 aqueous acetic acid (3×20 ml) and lyophilized. The crude material was chromatographed on a Sephadex SPC-25 column (60 cm×2.5 cm), equilibrated with 0.2M NH OAc, pH 5.25 at a flow rate of 85 ml/h with a fraction size of 10 ml. Fractions 130–153 were pooled and lyophilized to give 40 mg of material; $R_f 0.32$ (C); Amino acid analysis: Acid hydrolysis: Arg, 1.02; Lys, 0.98; Asp, 1.08; Val, 1.03; Tyr, 0.93; Gly, 0.95; Carboxypeptidase A hydrolysis: trace (<3 percent) of Tyr and Gly; FAB/MS MH+=719; HPLC: $C_{18}$-μBondapak, 2 ml/min, 214 nm, 10 percent methanol/0.02M KH$_2$PO$_4$, pH 3.5, retention time 60.26 min.

EXAMPLE XXVII

FMOC-Glu(OtBu)-Tyr(Bzl)-OBzl (29). FMOC-Glu(0-t-Bu) (4.25 g: 10 mmol) was dissolved in ethylacetate (25 ml) and cooled down 10°–15° C. Isobutylchloroformate (1.5 ml; 11 mmol) was added slowly with stirring. In a separate flask, TsOH Tyr(Bzl)-OBzl (5.3 g; 10 mmol) was dissolved in dimethylformamide (25 ml) and cooled down to $-15°$ C. N-methylmorpholine (1.2 ml; 11 mmol) was added dropwise with stirring. Both cooled solutions were combined and stirred for 5 h at ambient temperature. The solvent was removed under reduced pressure and the residue was dissolved in ethylacetate (200 ml), washed with 0.05N-hydrochloric acid (3×50 ml), water (50 ml), saturated sodium bicarbonate solution (3×50 ml) and water (50 ml) and anhydrous sodium sulfate. The drying agent was removed by filtration and the solvent was removed under reduced pressure. The residue was recrystallized from ethylacetate/petroleum ether to give 6.18 g (80 percent) of 29, m.p. 72°–76° C.

Anal. calcd for $C_{47}H_{47}N_2O_8$: C, 73.51; H, 6.16; N, 3.64. found: C, 73.09; H, 6.39; N, 3.45.

EXAMPLE XXVIII

FMOC-Asp(OBzl)-Glu(O-tBu)-Tyr(Bzl)-OBzl (30). FMOC-Asp(OBzl) (4.45 g; 10 mmol) was dissolved in ethyl acetate (30 ml) and cooled down to −15° C. Isobutylchloroformate (1.5 ml; 11 mmol) was added to the solution, followed by N-methylmorpholine (1.2 ml; 11 mmol). FMOC-Glu(O-t-Bu)-Tyr(Bzl)-OBzl (29) (6 g; 7.8 mmol) was treated with 10% piperidine in dimethylformamide (100 ml) for 1 h. The solvent was removed under reduced pressure and the residue was dissolved in dimethylformamide (30 ml) and added to the first solution at −15° C. The reaction mixture was stirred overnight at ambient temperature. Solids were removed by filtration and under reduced pressure. The residue was dissolved in ethylacetate (150 ml) and the insoluble material was removed by filtration. The organic solution washed with 0.05N hydrochloric acid (3×40 ml), water (40 ml) and dried over anhydrous sodium sulfate. The drying agent was removed by filtration and the filtrate evaporated under reduced pressure. The residue was crystallized from ethylacetate/petroleum ether to give 5.5 g (72 percent) of 30, m.p. 96°–99° C.

Anal. calcd for $C_{58}H_{59}N_3O_9$: C, 71.47; H, 6.10; N, 4.31. found: C, 71.12; H, 6.06; N, 4.64.

EXAMPLE XXIX

FMOC-Lys(Boc)-Asp(Bzl]Glu(O-t-Bu)-Tyr(Bzl)-OBzl (31). FMOC-Lys(Boc) (2.34 g; 5 mmol) was dissolved in ethylacetate (20 ml) and cooled to −15° C. Isobutylchloroformate (0.75 ml; 5.5 mmol) was added to the solution, followed by N-methylmorpholine (0.6 m; 5.5 mmol). In a separate flask, FMOC-Asp(OBzl)-Glu(O-t-Bu)-Tyr(Bzl)-OBzl (3.95 g; 4.05 mmol) was treated with 10 percent piperidine in dimethylformamide (100 ml) for 1 h. The solvent was removed under reduced pressure and the residue was dissolved in dimethylformamide (25 ml) and added to the first solution at −15° C. The mixture was stirred overnight at ambient temperature. Solids were removed by filtration and the residue was dissolved in ethylacetate (200 ml). Insoluble material was removed by filtration and the filtrate was washed with 0.05N hydrochloric acid (3×50 ml) and water (40 ml) and dried over anhydrous sodium sulfate. The drying agent was removed by filtration and the filtrate evaporated down to dryness under reduced pressure. The residue was crystallized from ethylacetate/ diethylether to give 3.45 g (70 percent) of 31, m.p. 145°–149° C.

Anal. calcd for $C_{69}H_{79}N$ 5.75: C, 68.02; H, 6.54; N, 5.75. found: C, 68.14; H, 6.74; N, 5.74.

Amino acid analysis: Asp, 1.05; Glu, 1.02; Tyr, 0.87; Lys, 1.05.

EXAMPLE XXX

FMOC-Lys(HCl)-Asp(OBzl)-Glu-Tyr(Bzl)-OBzl (32). FMOC-Lys (Boc)-Asp(OBzl)-Glu(OtBu)-Tyr(Bzl)-OBzl (31) (3.4 g; 2.79 mmol) was treated with 4N hydrochloric acid in dioxane (50 ml) for 1 h. The solvent was removed under reduced pressure and the residue triturated with ether (200 ml). The resulting solid was collected by filtration to give a white product. This material was recrystallized from ethylacetate/methanol/ diethylether and dried over $P_2O_5$ under reduced pressure to give 2.85 g of product (32). pmr showed absence of Boc- and t-Bu- groups.

EXAMPLE XXXI

FMOC-cyclo(Lys-Asp(OBzl)-Glu)-Tyr(Bzl)-OBzl (33). FMOC-Lys(HCl)-Asp(OBzl)-Glu-Tyr(Bzl)-OBzl (32) (1.45 g; 1.27 mmol) was dissolved in dimethylformamide (600 ml). The pH of the solution was adjusted to 7.5 with diisopropylethylamine. The mixture was cooled to −25° C. and diphenylphosphorylazine (0.3 ml) was added slowly with stirring and the resulting mixture was stirred at 4° C. for 7 days. The solvent was removed under reduced pressure and the residue was crystallized from N-methyl pyrrolidone/water to give 0.71 g of 33; $R_f$ 0.82 (D).

EXAMPLE XXXII

Cyclo-(Lys-Asp(OBzl)-Glu)-Tyr(Bzl)-OBzl. (34) FMOC-cyclo(Lys-Asp(OBzl)-Glu)-Tyr(Bzl)-OBzl (33) (0.71 g) was treated with 10 percent piperidine/dimethylformamide (20 ml) for 1 h. The solvent was removed under redcued pressure and the residue was triturated with ether. The solid was filtered and dried under reduced pressure to give 0.47 g of 34 as a white solid; $R_f$ 0.46 (D); Amino acid analysis: Lys, 1.06; Asp, 1.01; Glu, 1.02; Tyr, 0.90.

EXAMPLE XXXIII

Z-Arg(Z,Z)-cyclo(Lys-Asp(OBzl)-Glu)-Tyr(OBzl (35). Cyclo(Lys-Asp(OBzl)-Glu)-Tyr(Bzl)-OBzl (34) (470 mg; 0.5 mmol) was dissolved in dimethylformamide (5 ml). Tri-Z-Arginine (576 mg; 1 mmol), dicyclohexylcarbodiimide (206 mg; 1 mmol) and 1-hydroxybenzotriazole hydrate (153 mg; 1 mmol), each dissolved in dimethylformamide (5 ml), were added to the first solution and the reaction stirred overnight. Dimethylformamide (30 ml) and methanol (20 ml) were added to the reaction mixture and the mixture was warmed until all the solid went into solution. The solution was cooled to 4° overnight. The resulting solid was filtered off, washed with ethylacetate (2×10 ml) and diethylether (2×10 ml) and dried under reduced pressure to give 486 mg of 35 as an off-white solid which was used without further purification.

EXAMPLE XXXIV

Arg-cyclo(Lys-Asp-Glu)-Tyr (3). The protected pentapeptide, Z-Arg(Z,Z)-cyclo(Lys-Asp(OBzl)-Glu)-Tyr(Bzl)-OBzl (35) (340 g) and Pd-black (500 mg) were placed in a flask. Formic acid in methanol (5 percent, 40 ml) was added dropwise under a nitrogen atmosphere. The reaction mixture was stirred for 48 h. The catalyst was removed by filtration washed with methanol (3×30 ml) and water (20 ml). The combined filtrates were evaporated under reduced pressure. The residue was dissolved in water (50 ml) and lyophilized. The lyophilized sample (185 mg) was placed on a Sephadex SPC-25 Column (60 cm×20 cm) and eluted with 0.05M NH₄OAc, pH 4.75. The flow rate was 80 ml/h and fractions of 10 ml were collected. After 40 fractions, the buffer was changed to 0.05 M NH OAc, pH 6.98. Fractions 80–100 were collected and lyophilized. The residue was desalted on a Sephadex G-10 Column (100 cm×2.5 cm), eluted with water. The flow rate was 25 ml/h and fractions of 9 ml were collected. Fractions 24–30 were pooled and lyophilized to give 125 mg of producet; $R_f$ 0.22 (B); FAB/Ms:MH+ 692; Amino acid analysis: acid hydrolysis: Arg, 1.01; Lys, 0.99; Asp 1.00; Val 1.02; Tyr, 0.98; Leucine amino peptidase: Arg, 1.04; Asp, 0.96;. Tyr, 1.00. HPLC: $C_{18}$-μBondapak, 5 percent acetonitrile in 1 percent aqueous phosphoric acid, pH 2.9, 2 ml/min, 214 nm, retention time 6.38 min.

EXAMPLE XXXV

Aspartic acid-α-benzyl ester-β-t-butyl ester (36). To a solution of Boc-Asp-OBzl (2.60 g, 8 mmol) in t-butyl acetate (120 ml) was added perchloric acid (70 percent, 1.25 g). The solution was stirred for 4 days at 23° C. The mixture was diluted with ethylacetate (120 ml) and saturated sodium bicarbonate (175 ml) was slowly added. As the foaming subsided, solid sodium bicarbonate was added until the solution reached pH 7.5. The aqueous phase was separated and extracted several times with ethylacetate. The organic phases were combined and dried with anhydrous sodium sulfate. The drying agent was removed by filtration and the solvent was removed under reduced pressure to give 1.6 g (71%) of 36 as a semi-solid material.

EXAMPLE XXXVI

FMOC-Lys(Boc)-Asp(O-t-Bu)-OBzl (37). To a solution of FMOC-Lys(BOC) (11.07 g, 23.7 mmol) in 1:1, dimethylformamide:ethylacetate (50 ml) was added N-methylmorpholine (2.04 g, 2.37 mmol). The mixture was cooled to -20° C. to −25° C. Isobutyl chloroformate (3.23 g, 23.7 mmol. and the reaction mixture was stirred for 30 min. To this was added a solution of Asp (o-t-Bu)OBzl (36) (6.3 g, 22.6 mmol) in 1:1 dimethylformamide:ethylacetate. After the mixture was stirred for 30 min. at −20° C. the cooling was removed and the solution allowed to rise to ambient temperature. The reaction mixture was diluted with ethylacetate and poured into a saturated solution of sodium bicarbonate. The aqueous phase was extracted 3 times with ethyl acetate (75 ml). The organic phases were combined and washed with a saturated sodium chloride solution. The organic phase was separated and dried with anhydrous sodium sulfate. The solvent was removed under reduced pressure to give 18.6 g. crude product. This material was chromatographed on silica gel 5 percent acetone in chloroform to give 3.2 g of 37 (76 percent) which was used without further characterization.

EXAMPLE XXXVII

FMOC-Lys(Boc)-Asp(O-t-Bu) (40). To a solution of FMOC-Lys(Boc)-Asp(O-t-Bu)-OBzl (37) (5.0 g, 6.9 M) in dimethylformamide (50 ml) was added 10 percent Pd/C (500 mg). The mixture was hydrogenated for 5 hrs at 50 psi H₂. The solids were removed by filtration and the solvents removed under reduced pressure. This material was chromatographed on silica gel, eluting with acetone/methylene chloride/acetic acid 25/74/1 to give 4.3 g (98 percent) of 40 which was used without further characterization.

EXAMPLE XXXVIII

FMOC-Lys(Boc)-Asp(O-t-Bu)-Val-Tyr-OBzl (41). To a solution of FMOC-Lys(Boc)-Asp(O-t-Bu) (4.2 g, 6.6 mmol) in ethylacetate (30 ml) was added N-methylmorpholine (0.665 g, 6.6 mmol). The solution was cooled to −15° C. to −20° C. To this solution was added isobutyl chloroformate (0.899 g, 6.6 mmol). The mixture was stirred for 10 min. and a solution of HCl Val-Tyr-OBzl (2.68 g, 6.6 mmol) dissolved in 20 ml of a 1:1 solution of dimethyl formamide and ethylacetate and neutralized with N-methylmorpholine (0.665, 6.6 mmol) was added. The mixture was stirred for 1 hr at −20° C. and the temperature was allowed to rise to ambient. The mixture was diluted with ethylacetate (200 ml) and washed twice with a solution of saturated sodium bicarbonate and once with a solution of saturated sodium chloride. The organic phase was dried with anhydrous sodium sulfate. The drying agent was removed by filtration and the solvent removed under reduced pressure. The residue was crystallized from ethylacetate to give 4.98 g (76 percent) of 41.

Anal. calcd for $C_{55}H_{69}N_5O_{12}$: C, 66.58; H, 7.01; N 7.06. found: C, 66.11; H, 7.34; N 6.77.

EXAMPLE XXXIX

FMOC-Lys-(HCl)-Asp-Val-Tyr-OBzl (42). A solution of 4.5N HCl in dioxane (40 ml) was added to FMOC-Lys(Boc)-Asp(O-t-Bu)-Val-Tyr-OBzl (41) (4.5 g, 45 mmol) and stirred for 3 hr at ambient temperature. The solvent was removed under reduced pressure to give (100 percent) of 42 as a white solid which was used without further purification.

EXAMPLE XL

FMOC-cyclo-(Lys-Asp)-Val-Tyr-OBzl (43). To a solution of FMOC-Lys-(HCl)-Asp-Val-Tyr-OBzl (4.0 g, 4.8 mmol) and diphenylphosphorylazine (1.58 g, 5.7 mmol) in dimethylformamide (1000 ml) at ambient temperature was added triethylamine (a few drops) to adjust the pH to 7.2. The mixture was allowed to stand for two days at −15° C. The solvent was removed under reduced pressure and the product precipitaited by trituration with water. After filtering and drying, 3.8 g of 43 was isolated. This materials was used without further characterization or purification.

EXAMPLE XXXXI

Cyclo-(Lys-Asp)-Val-Tyr-OBzl (44). A solution of FMOC-cyclo(Lys-Asp)-Val-Tyr-OBzl (43) (3.6 g, 4.4 mmol) in 20 percent (v/v) piperidine/dimethylformamide (30 ml) was stirred for 3 hrs at ambient temperature. The solvent was removed under reduced pressure and the product was dissolved twice in dimethylformamide (15 ml) and the solvent removed under reduced pressure to remove all traces of piperidine to yield 2.62 g of 44. This material was used without further characterization or purification.

EXAMPLE XLII

Z-Arg(HCl)-cyclo-(Lys-Asp)-Val-Tyr-OBzl (45). To a solution of Z-Arg (HCl) (1.66 g, 4.8 mmol) and N-methylmorpholine (0.486 g, 4.8 mmol) in dimethylformamide (10 ml) at −20° C. was added isobutyl chloroformate (0.656 g, 4.8 mmol). The mixture was stirred for 30 min. To the reaction mixture was added dropwise, a solution of cyclo-(Lys-Asp)-Val-Tyr-OBzl (44) (2.62 g, 4.4 mmol) in dimethylformamide (40 ml). The mixture was stirred for 1 hr at −20° and the temperature was then allowed to rise to ambient. The mixture was added to water (200 ml) and the product precipitated as a white solid. The solid was removed by filtration, washed with ether and dried to give 3.95 g of 45. This material was used without further characterization or purification.

EXAMPLE XLIII

Arg-cyclo-(Lys-Asp)-Val-Tyr (4). To a solution of Z-Arg(HCl)cyclo-(Lys-Asp)-Val-Tyr-OBzl (3.0 g, 3.4 mmol) in 90 percent acetic acid (30 ml) was added 10 percent Pd/C (300 mg). The mixture was hydrogenated for 72 hrs with 50 psi $H_2$. The reaction mixture was filtered and the filtrate lyophilized. The crude material was dissolved in 0.01M $NH_4OAc$ at pH 5.00 and chromatographed on a 2.5×90 cm column packed with Sephadex SPC-25, eluted with a gradient from 0.01M $NH_4OAc$ pH 5.00 to 0.2M $NH_4OAc$ pH 5.00 to give 120 mg of 4. $R_f$ 0.14 (A); POS F.A.B. MH+ M W 662; NEG F.A.B. MH−MW 660; Amino acid analysis: Arg (1.00), Lys (0.68), Asp (0.60), Val (1.02), Tyr (1.01), 63% peptide. Leucine aminopeptidase, Arg (1.00), Lys (0.02), Asp (0.04), Val (1.05), Tyr (1.03).

EXAMPLE XLIV

Cyclic-GMP Assay

This assay measures the ability of the test peptide to bind to the cell membrane receptor of the intact CEM cell and selectively stimulate production of cyclic-GMP, as does thymopoietin itself.

The CEM cell line was obtained from the American Type Culture Collection and was cultured in RPMI-1640 medium supplemented with 10% heat-inactivated fetal bovine serum, 10% heat-inactivated horse serum, 2mM L-glutamine, and 50 g/ml gentamycin at 37° C. in a humid atmosphere containing 5 percent $CO_2$, to a final density of 3–4×106 cells/ml. At this concentration, the cells were in the early stationary phase of the growth curve and were judged greater than 90% viable by trypan blue exclusion. The cells were grown for four days and harvested. After harvesting, the cells were washed three times in PBS and were resuspended in RPMI-1640 medium at a concentration of $3.12 \times 10^7$ cells/ml. After the cells had been allowed to equilibrate at 37° C. for 30 min, various concentrations of the test peptides were added in a volume of 25 μl of medium to 1 ml of cells, the initial concentration of test compound added being selected to yield the desired final concentration of test peptide in the medium. The test peptide was mixed instantly with the cell suspension. The incubation was allowed to proceed in a shaking water bath at 37° C. for 4–5 min and was then terminated by addition of ice-cold trichloroacetic acid (10%; 1 ml).

The cells in TCA were then homogenized and sonicated to release cyclic nucleotide. The resulting suspension was centrifuged at 3000 g for 20 min at 4° C. and the resulting precipitate was dissolved in 0.1N NaOH and sonicated for a further 30 minutes, after which the protein content was determined by the method of Cadman, et al., Anal. Biochem., 96, 21–23 (1979). The TCA was removed from the supernatant fraction by extracting four times with 5 ml of water-saturated diethyl ether. After the final extraction, the remaining traces of ether were removed from the supernatant fraction by heating it for 10 min in a 50° C. water bath. After lyophilization of the extracted supernatant fraction, it was reconstituted in 50 mM acetate buffer, ph 6.2, for radioimmunoassay of cyclic nucleotide using the assay kit NEX-133, New England Nuclear, Boston, MA 02113.

A conventional competition radioimmunoassay against radio labelled cyclic GMP was conducted to determine the amount of cyclic GMP induced by each concentration of test peptide. Peptides 1, 2, and 4 demonstrated thymopentin-like activity in this assay while peptide 3 was inactive.

EXAMPLE XLV

Receptor Assay

This assay measures the ability of the test peptide to compete with labelled thymopoeitin to bind to the isolated thymopoietin cell surface receptor protein from CEM cells.

Materials—CEM cell lines were obtained from the American Type Culture Collection. 3-Nitro-2-pyridine sulfonyl chloride and 2-pyridinethiol 1-oxide were provided by Dr. Rei Matsueda, Sanyo Laboratories, Tokyo. RPMI-1640, fetal bovine serum and L-glutamine were obtained from Gibco, gentamycin from Schering, and lectin-coupled agarose beads from Vector Laboratories. Sephadex was purchased from Pharmacia Fine Chemicals. and human IgG from Miles Laboratories. All other chemicals were purchased from common commercial sources and were of reagent grade. Rabbit anti-thymopoeitin antibody and ubiquitin were produced following known techniques.

The abbreviations used are: PBS, phosphate-buffered saline; TCA, trichloroacetic acid; SDS, sodium dodecylsulfate; Con A, concanavilin A; TP, thymopoietin; PEG, polyethylene glycol; BSA, bovine serum albumin; I.P., intraperitoneal; PMSF, phenyl methyl sulfonyl fluoride; FTS, facteur thymique serique; CRF, corticotropin-releasing factor; ACTH, adrenocorticotropic hormone; Hepes, N-2-hydroxyethylpiperazine N-2-ethane-sulfonic acid.

Preparation of Membrane Glycoprotein—The CEM human lymphoid cell line was cultured in RPMI-1640 supplemented with 10 percent heat-inactivated fetal bovine serum, 2 mM L-glutamine and 50 μg/ml gentamycin at 37° C. in a humid atmosphere containing 5 percent $CO_2$, to a final density of $3-4 \times 10^6$ cells/ml. At this concentration, cells were in the early stationary phase of the growth curve and were judged greater than 90 percent viable by trypan blue exclusion.

Membrane glycoproteins were prepared by a modification of the technique of Hedo, et al., Biochem, 20, 3385–3393 (1981). The cells were washed once with PBS and were suspended in 40 percent sucrose, 50 50 mM Hepes, 1 percent EDTA, 0.1 percent O-phenanthroline, and 1 mM PMSF (in methanol), pH 7.8, and homogenized in a glass homogenizer at room temperature. The total suspension was then subjected to sonication by a cell disruptor sonicator with a cup horn attachment (Model W-225R) at 35° C. for 10 min. The suspension was centrifuged at 600×g for 10 min at 4° C. in a Sorval GLC-3 centrifuge, and the supernatant was recentrifuged at 20,000×g in a Sorval 5B centrifuge at 4° C. for 3 min. The crude membrane fraction obtained from this pellet was suspended in 50 mM Hepes, 10 mM $MgSO_4$, and 1 mM PMSF, pH 7.8, at a final protein concentration of 5 mg/ml. Solubilization of protein was performed by stirring the suspension for 2 h at 25° C. in the presence of 1 percent Triton X-100 (final concentration) and 0.1 percent brij-96 (polyoxyethylene 10, oleyl ether) (final concentration). The suspension was centrifuged at 200,000×g for 2 h at 4° C., and the supernatant was stored at −70° C. Soluble protein concentration was measured according to the technique of Cadman, et al., using BSA as a standard and buffer as a control.

Wheat germ agglutinin or ricinus communis agglutinin-I was used for purification of the receptor protein. All lectin beads were stored at 4° C. with their corresponding monosaccharide inhibitors (300 mM).

For each purification 2 ml of lectin-agarose was packed into a 1 cm diameter column and washed at room temperature with 25 ml of 0.15M NaCl, 50 mM Hepes, 0.1 percent Triton X-1 and 0.01 percent SDS, pH 7.8.

The columns were washed with 200 ml of 0.15M NaCl, 50 mM Hepes and 0.1 percent Triton X-100, pH 7.8, followed by a final wash of this buffer containing 10 mM $MgSO_4$. PMSF (1 mM) was added to all the buffer systems. Solubilized membrane proteins (∼ 10 mg) were recycled five times through individual columns. The column was then washed with 100 ml of 0.15M NaCl, 50 mM Hepes, 10 mM MgSO and 0.1 percent Triton X-100, pH 7.8, at 4° C. Monosaccharide inhibitors, at a concentration of 400 mM in 3 ml washing buffer, were used for individual column elutions; N-acetyl glucosamine for wheat germ agglutinin and β-methyl D-galactoside for ricinus communis agglutinin-I. The monosaccharides were applied to the column, which was stopped for 30–40 min to permit equilibration and then eluted further. The protein eluate was dialyzed against 500 ml of 50 mM Hepes, 10 mM $MgSO_4$ and 0.1 percent Triton X-100, pH 7.8, at 4° C.

Preparation of Radiolabelled Thymopoietin—Thymopoietin was dissolved in 0.2M sodium carbonate-bicarbonate buffer, pH 9.8, to obtain reactive amino groups. 3-nitro-2-pyridine sulfonyl chloride in dioxane (10:1 moles) was added to the thymopoietin solution and stirred for 5 h at 20° C. After the addition of water the insoluble material was centrifuged. The protected peptide was purified using Sephadex G-25 chromatography followed by digestion with post-proline cleaving enzyme to remove the $NH_2$-terminal blocked proline. Methyl 3,5 di[$^{125}$I]iodohydroxybenzimidate (4000 Ci/mM) was obtained at a concentration of 5.5 mCi/ml in methanol and was evaporated to dryness. The iodinated imidoester (1.4 nM) was reacted with protected thymopoietin (5 μg; 0.9 nM) according to the method of Wood, et al., Anal. Biochem., 69, 339–349 (1975), with the following modifications. The reaction was carried out in 500 μl of 0.16M borate buffer, pH 9.1, for 24 h at 4° C. The reaction was stopped by the addition of 500 μl of 2M citrate phosphate buffer, pH 5.5, at 4° C. The sample was chromatographed on a Biogel P-10 column in sodium pyrophosphate, pH 7.5 (15 drops/fraction), at 4° C. to separate the free iodine.

The iodinated peptide was dissolved in water and treated with 2-pyridinethiol 1-oxide (10:1 moles) for 5 h at room temperature to remove the protecting groups. The deprotected labelled peptide was purified on a Biogel P-10 column. Three radioactive peaks were obtained, the first two of which were immunoactive with rabbit antithymopoietin antibody. The first peak was then applied to a 1×60 cm column of DEAE-Sephedex A-25 that had been equilibrated with 50 mM Tris buffer, pH 7.0. The iodination mixture was eluted with this buffer using a linear gradient of increasing ionic strength from the equilibration concentration up to 1.0M. The radioactivity of each fraction was determined using an LKB 1280 Ultra gamma spectrometer.

Fractions with peak radioactivity from each purification scheme were analyzed for binding with excess antithymopoietin antibody. Fractions from peak II (fractions 35–45) of the DEAE-Sephedex A-25 column showed the highest specific binding and were used subsequently in the radioreceptor assay.

Iodinated thymopoietin retained biological activity as determined by assessing its effect in a neuromuscular assay (Goldstein, Nature, 247, 11–14 (1974)) and its effect on the synthesis of cyclic GMP by CEM cells.

Binding Assay—The assay buffer was prepared by adding 12 g Hepes, 1.2 g $MgSO_4$ and 1.2 g BSA to 1000 ml of glass distilled water. A pH of 7.65 was obtained using 1N NaOH. The stock standard solution was made using assay buffer and was used for one week. The assay was performed in 12×75 mm glass test tubes by the addition of 100 μl of standard solution, 25 μl of receptor protein (150–200 μg/ml), 25 μl $^{125}$I-TP (80,000 cpm)) 20 μl of 1 percent Triton X-100, and the volume was made up to 200 μl with assay buffer. After incubation for 18 h at 4° C., 200 μl of human IgG (1.5 mg/ml) (as carrier) and 200 μl of 35 percent PEG-8000 in PBS, pH 7.56, were added, mixed, and incubated for 30 min on ice. The tubes were centrifuged and the residue was washed with 10 percent PEG in PBS, pH 7.3, and counted in an LKB-gamma counter.

The radioactivity in the precipitate in the presence of 1 mg/ml nonradioactive thymopoietin was taken to represent nonspecific binding. TCA was added to the supernatant (final concentration 5 percent) and precipitable radioactivity was measured. At all times this exceeded 95 percent, indicating minimal release of free $^{125}$I from the tracer.

Competition Experiments—Following the above binding assay procedure, $2.3 \times 10^{-10}$M of $^{125}$I-Tp was incubated with 4 μg of receptor protein and test peptide together with the same concentration of the thymopoietin 37–45 nonapeptide (H-VAL-GLU-LEU-TYR-LEU-GLN-SER-LEU-TNR-OH). The incubation was continued for 12 h, after which free and bound $^{125}$I-Tp were determined as above. The nonapeptide is used to block an adjacent receptor site on the receptor protein. If this adjacent receptor site is not blocked, some labelled TP can bind to the receptor protein through this site even if the thymopentin receptor site is blocked by the test peptide. Such binding is unrelated to the activity of the test peptide and (if not blocked by the TP 37–45 nonapeptide) would yield inaccurate results.

The following representative compounds of the invention caused displacement at least 50% of that caused by thymopoietin self-displacement at equivalent concentrations:

Cyclo-(ARG-LYS-ASP-VAL-TYR), peptide 1;
Cyclo-(ARG-LYS-ASP-VAL-TYR-GLY), peptide 2; and
H-ARG-cyclo-(LYS-ASP)-VAL-TYR-OH, peptide 4.

Peptide 3 [H-ARG-cyclo-(LYS-ASP-GLY)-TYR-OH] caused no detectable displacement.

For comparison, other peptides such as insulin, glucagon, growth hormone, somatostatin, β-endorphin, FTS, ACTH, CRF, and ubiquitin caused no detectable displacement.

The above Examples have been presented for illustrative purposes only and not to limit the scope of the present invention, which scope is set out in the following claims.

What is claimed is:

1. A peptide having the formula:

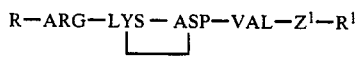

or

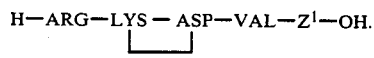

or a pharmaceutically-acceptable acid- or base-addition salt thereof, wherein:
R is H, loweralkyl, formyl or loweralkanoyl;
W is LYS, PRO, dehydro-PRO, or AIB;
Z is TYR, TYR-GLY, PHE, or PHE-GLY;
$Z^1$ is TYR or PHE;
$R^1$ is OH or $NR^2R^3$; and
$R^2$ and $R^3$ are each independently selected from H or loweralkyl.

2. The peptide of claim 1 which is

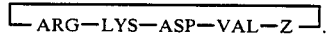

3. The peptide of claim 1 which is

H—ARG—LYS—ASP—VAL—$Z^1$—OH.

4. A peptide having the formula cyclo-(ARG-LYS-ASP-VAL-TYR) or a pharmaceutically-acceptable acid- or base-addition salt thereof.

5. A peptide having the formula cyclo-(ARG-LYS-ASP-VAL-TYR-GLY) or a pharmaceutically-acceptable acid- or base-addition salt thereof.

6. A peptide having the formula H-ARG-cyclo-(LYS-ASP)-VAL-TYR-OH or a pharmaceutically-acceptable acid- or base-addition salt thereof.

7. A pharmaceutical composition comprising an effective T cell inducing amount of a peptide of claim 1 in admixture with a pharmaceutically acceptable carrier.

8. A method for treatment of a condition resulting from relative or absolute T cell deficiency in a subject having such a condition which comprises administering to the subject a therapeutically-effective amount of a peptide of claim 1.

9. A method for inducing lymphopoietic stem cells of a subject to develop the characteristics of thymus-derived lymphocytes which comprises administering to the subject an effective inducing amount of a peptide of claim 1.

* * * * *